US011246491B2

(12) United States Patent
Yang

(10) Patent No.: US 11,246,491 B2
(45) Date of Patent: Feb. 15, 2022

(54) PORTABLE BREAST LIGHT ASSEMBLY

(71) Applicant: Power Productions Group LLC., Coral Gables, FL (US)

(72) Inventor: Lin Yang, Neuss (DE)

(73) Assignee: Power Productions Group LLC., Miami, FL (US)

( * ) Notice: Subject to any disclaimer, the term of this patent is extended or adjusted under 35 U.S.C. 154(b) by 234 days.

(21) Appl. No.: 15/598,442

(22) Filed: May 18, 2017

(65) Prior Publication Data
US 2019/0261864 A1 Aug. 29, 2019

(51) Int. Cl.
*A61B 5/00* (2006.01)

(52) U.S. Cl.
CPC .... *A61B 5/0091* (2013.01); *A61B 2560/0431* (2013.01)

(58) Field of Classification Search
CPC .......... A61B 2560/0431; A61B 5/0091; A61B 5/404
See application file for complete search history.

(56) References Cited

U.S. PATENT DOCUMENTS

| 4,286,602 | A | 9/1981 | Yang | |
|---|---|---|---|---|
| RE33,324 | E | 6/1990 | Landry | |
| 5,342,617 | A * | 8/1994 | Gold | A61K 8/345 424/405 |
| D362,910 | S | 10/1995 | Creaghan | |
| 5,683,350 | A | 11/1997 | Paul et al. | |
| 5,799,656 | A | 9/1998 | Alfano et al. | |
| 6,148,223 | A | 11/2000 | Davis et al. | |
| 6,230,046 | B1 | 5/2001 | Crane et al. | |
| 6,923,762 | B1 | 8/2005 | Creaghan, Jr. | |
| 7,155,273 | B2 | 12/2006 | Taylor | |
| 7,431,695 | B1 | 10/2008 | Creaghan | |
| 8,032,205 | B2 | 10/2011 | Mullani | |
| 8,231,542 | B2 | 7/2012 | Keith et al. | |
| 8,388,523 | B2 | 3/2013 | Vivenzio et al. | |
| 8,463,364 | B2 | 6/2013 | Wood et al. | |
| 8,838,210 | B2 * | 9/2014 | Wood | A61B 5/0059 600/476 |
| 9,044,207 | B2 | 6/2015 | Goldman et al. | |
| 9,061,109 | B2 | 6/2015 | Wood et al. | |
| 9,186,063 | B2 | 11/2015 | Goldman et al. | |
| 9,492,117 | B2 | 11/2016 | Goldman et al. | |
| 2005/0168980 | A1 * | 8/2005 | Dryden | A61B 5/0059 362/230 |

(Continued)

*Primary Examiner* — Keith M Raymond
*Assistant Examiner* — Milton Truong
(74) *Attorney, Agent, or Firm* — Albert Bordas, P.A.

(57) ABSTRACT

A portable breast light assembly, having a housing with a sidewall. An electrical assembly has a control panel having a power switch, a timer controller, an intensity controller, a screen, and at least one light source to emit visible light at a predetermined wavelength. The present invention further has a cap assembly. The timer controller controls at least one range of operating time. The intensity controller controls at least one level of light intensity. The electrical assembly has a sensor. The sensor is connected to circuitry that is connected to the at least one light source. The cap assembly has a cover. The cover contacts the sensor. The light emitted by the at least one light source illuminates a breast when the cover is biased against the breast with a predetermined force.

1 Claim, 4 Drawing Sheets

(56) References Cited

U.S. PATENT DOCUMENTS

| | | | |
|---|---|---|---|
| 2006/0287696 A1* | 12/2006 | Wright | A61N 5/0613 607/88 |
| 2008/0103563 A1* | 5/2008 | Powell | A61N 5/0616 607/89 |
| 2010/0044589 A1* | 2/2010 | Garcia | G01N 21/6447 250/492.1 |
| 2010/0196343 A1* | 8/2010 | O'Neil | A61B 18/203 424/94.4 |
| 2010/0274329 A1* | 10/2010 | Bradley | A61N 1/328 607/90 |
| 2011/0190638 A1* | 8/2011 | Devlin | A61B 5/0091 600/476 |
| 2012/0101342 A1 | 4/2012 | Duffy et al. | |
| 2012/0101343 A1 | 4/2012 | Duffy et al. | |
| 2012/0165710 A1* | 6/2012 | Nichols | A61H 7/005 601/72 |
| 2015/0094662 A1 | 4/2015 | Lee et al. | |

\* cited by examiner

PORTABLE BREAST LIGHT ASSEMBLY

BACKGROUND OF THE INVENTION

1. Field of the Invention

The present invention relates to light assemblies, and more particularly, to portable light assemblies to examine breasts.

2. Description of the Related Art

Applicant believes that one of the closest references corresponds to U.S. Pat. No. 4,286,602 issued to Robert Guy on Sep. 1, 1981 for Transillumination diagnostic system. However, it differs from the present invention because Guy teaches a transillumination system for carrying out breast examination to determine the existence of a carcinoma and other pathological conditions. The system includes a portable lightbeam projector in the form of a gun which houses a low-voltage, high wattage lamp whose reflector is sealed to the end of the gun barrel to project a light beam therethrough, the gun grip having a trigger-finger switch for the lamp. The gun operates in conjunction with a camera assembly formed by a tripod-mounted bracket having a camera secured to one end, the camera being trained on a guide fixture attached to the other end. The fixture is adapted to engage the rib cage of the patient just above the breast and to present the breast to the camera lens at a fixed location. The shutter mechanism of the camera is coupled to a remote actuator operable by one hand or foot of the operator. Thus an operator who holds the gun in his hand is able without assistance to orient the light beam relative to the patient's breast and to activate the trigger finger switch to transilluminate and observe the internal structure of interest, the operator also being in a position to take a well-focused picture of the transilluminated breast without having to observe the image through the range finder of the camera.

Applicant believes that another reference corresponds to U.S. Pat. No. 5,683,350 published on Nov. 4, 1997 to Paul et al. for Oral transluminating device. However, it differs from the present invention because Paul et al. teach a portable hand-held transluminating wand, which includes a hand-grip portion containing the power source and an illumination source at a narrow terminating end. The illumination source is enclosed by a slide-on transparent cover, which is shaped to permit insertion into a patient's mouth and placement against the roof of the mouth without discomfort. The translucent cover is tinted red to selectively provide light of a desired bandwidth beneficial to translumination of human tissue. The cover is clear in the region to be placed in contact with the roof of the mouth so that the light emitted in this region is not diffused but remains directed toward the roof of the mouth to facilitate translumination and frosted elsewhere to inhibit light leakage from the patient's mouth when closed about the device. The wand is constructed with a multi-position switch, which permits the illumination source to be turned off and on through levels of illumination.

Applicant believes that another reference corresponds to U.S. Pat. No. 5,799,656 issued to Alfano, et al. on Sep. 1, 1998 for Optical imaging of breast tissues to enable the detection therein of calcification regions suggestive of cancer. However, it differs from the present invention because Alfano, et al. teach a method for detecting the presence of one or more calcifications within a portion of a turbid medium, such as a breast tissue. According to one aspect, the method involves illuminating at least a portion of the turbid medium with light, whereby light emerges from the turbid medium consisting of a ballistic component, a snake-like component and a diffuse component, temporally and/or spatially gating the emergent light to preferentially pass the ballistic and/or snake-like components, using the temporally and/or spatially gated light to form an image of the illuminated portion of the turbid medium, and examining the image for the presence of one or more calcifications. Wavelength difference images may also be used to highlight tumors and calcification regions. The foregoing method may be used to form optical images of breast tissues, with the presence in such images of calcifications suggestive of cancer being used to identify the corresponding breast tissues as good candidates for biopsy and screening for tumors.

Applicant believes that another reference corresponds to U.S. Pat. No. 6,148,223 issued to Davis, et al. on Nov. 14, 2000 for Transilluminator device. However, it differs from the present invention because Davis, et al. teach a medical transilluminator device. The device includes a fiberoptic cable that is interconnected at one end to a fiberoptic illuminator. The opposite end of the cable is interengaged to a transilluminating spacer component that transmits light toward tissue being examined. A light intensity adjusting mechanism may be interengaged between the fiberoptic cable and the spacer component.

Applicant believes that another reference corresponds to U.S. Pat. No. 6,230,046 issued to Crane, et al. on May 8, 2001 for Optical imaging of breast tissues to enable the detection therein of calcification regions suggestive of cancer. However, it differs from the present invention because Crane, et al. teach a system and method for enhancing visualization of veins, arteries or other subcutaneous natural or foreign structures of the body and for facilitating intravenous insertion or extraction of fluids, medication or the like in the administration of medical treatment to human or animal subjects, which comprise a light source for illuminating or transilluminating the corresponding portion of the body with light of selected wavelengths and a low-level light detector such as an image intensifier tube (including night vision goggles), a photomultiplier tube, photodiode or charge coupled device, for generating an image of the illuminated body portion, and optical filter(s) of selected spectral transmittance which can be located at the light source(s), detector, or both.

Applicant believes that another reference corresponds to U.S. Pat. No. 7,155,273 issued to Geoffrey L. Taylor on Dec. 26, 2006 for Blanching response pressure sore detector apparatus and method. However, it differs from the present invention because Taylor teaches a portable, handholdable Blanching Response Tester apparatus (BRT) pressable against the skin of a human patient to provide an indication of a nonblanchable erythema indicative of an incipient pressure sore includes a housing having in a front end wall thereof an optically transmissive window and within the housing a broad-band light source electrically energizable to emit light including energy in the near infrared (0.8.mu. to 1.5.mu.) outwards through the window. A first, leading photodetector spaced laterally apart from the light source and a second, trailing photodetector spaced equidistant from the light source in an opposite direction have fields of view which include regions of the skin ahead of an behind a central area of the skin illuminated by the light source. Electronic signal processing circuitry within the BRT housing includes a pair of differential amplifiers having opposite pairs of inputs connected to the pair of photodetectors, one amplifier driving a first, "NO-GO" red, light-emitting diode mounted in an upper wall panel of the housing, and the other amplifier driving a second, "GO" green LED. When the BRT window is pressed against the skin and the light source energized, if light reflected from the skin by leading photodetector over a questionable area of the skin exceeds light reflected from a known healthy sample area of skin beneath the trailing photodetector the red, NO-GO LED is illuminated if the difference in light values exceeds a first threshold values signifying a pressure sore, and if light received by the trailing photodetector exceeds that received by the leading photodetector by a second threshold value, the green, GO LED is illuminated.

Applicant believes that another reference corresponds to U.S. Pat. No. 7,431,695 issued to Frank Creaghan on Oct. 7, 2008 for Neonatal transilluminator apparatus. However, it differs from the present invention because Creaghan teaches a transilluminator device for use with neonatal patients, which includes a power housing for providing power to the unit; a flexible cord, extending from the housing, and terminating in a small container for housing LED's; a plurality of red and white LED's containing the smaller housing, which are illuminated when power is provided to the LED's; the small housing positionable in the hands of a person, so that when a neonatal patient is placed in the person's hand the LED's will illuminate that portion of the neonatal person such as the arm, leg or other part of the anatomy in order to determine whether or not the physical conditions are normal or abnormal and to locate suitable veins for blood draws and therapy in an infant.

Applicant believes that another reference corresponds to U.S. Pat. No. 8,032,205 issued to Nizar A. Mullani on Oct. 4, 2011 for Transilluminator light shield. However, it differs from the present invention because Mullani teaches a transillumination that uses light to image tissues and organs, specifically the veins within the tissue. Strong ambient light hinders the imaging of veins and often, transillumination must be done in a dark or dim room. To enhance the capabilities of a transilluminator, a light shield is placed over the viewing area of the transilluminator so that turning off or dimming of ambient light is not necessary. For pediatric care, a frustroconical adapter attached to the bottom of the transilluminator. The adapter reduces the size of the viewing area.

Applicant believes that another reference corresponds to U.S. Pat. No. 8,231,542 issued to Keith, et al. on Jul. 31, 2012 for System for analyzing thermal data based on breast surface temperature to determine suspect conditions. However, it differs from the present invention because Keith, et al. teach a portable computing device or microprocessor/storage system including temperature sensors used to collect temperature readings of a breast tissue of a subject. The device would collect data from the sensors at regular time intervals over a period of time. All of the generated temperature data is stored in the portable computing or storage device. The sensors are placed on the greatest areas of interest on the breast, based on where most cancers develop, by using a sensor placeholder. The sensor placeholder would be lobate shaped, with the sensor placeholder aligning with the glandular regions of the breast where cancers are most likely to develop. The temperature data is then analyzed by one or more classifier systems and classified as either suspect or nonsuspect tissue.

Applicant believes that another reference corresponds to U.S. Pat. No. 8,388,523 issued to Vivenzio, et al. on Mar. 5, 2013 for Medical diagnostic instrument having portable illuminator. However, it differs from the present invention because Vivenzio, et al. teach a portable medical diagnostic instrument which includes an instrument head and a handle portion having an open-ended receiving cavity. A compact illuminator defined by a housing retaining a miniature light source and a power supply is releasably fitted within the open-ended receiving cavity of the handle portion wherein the light source of the illuminator is optically coupled with the instrument on assembly therewith. The handle portion can be integral with the instrument or releasably attached. The handle portion according to at least one version is made from a plastic or other suitable material, permitting disposability and/or single patient use. In one version, the handle portion is flexibly deformable, at least partially, to facilitate release of the portable illuminator.

Applicant believes that another reference corresponds to U.S. Pat. No. 8,463,364 issued to Wood, et al. on Jun. 11, 2013 for Vein scanner. However, it differs from the present invention because Wood, et al. teach a portable vein viewer apparatus which may be battery powered and hand-held to reveal patient vasculature information to aid in venipuncture processes. The apparatus comprises a first laser diode emitting infrared light, and a second laser diode emitting only visible wavelengths, wherein vasculature absorbs a portion of the infrared light causing reflection of a contrasted infrared image. A pair of silicon PIN photodiodes, responsive to the contrasted infrared image, causes transmission of a corresponding signal. The signal is processed through circuitry to amplify, sum, and filter the outputted signals, and with the use of an image processing algorithm, the contrasted image is projected onto the patient's skin surface using the second laser diode. Revealed information may comprise vein location, depth, diameter, and degree of certainty of vein locations. Projection of vein images may be a positive or a negative image. Venipuncture needles may be coated to provide visibility in projected images.

Applicant believes that another reference corresponds to U.S. Pat. No. 8,838,210 issued to Wood, et al. on Sep. 16, 2014 for Scanned laser vein contrast enhancer using a single laser. However, it differs from the present invention because Wood, et al. teach a miniature Vein Enhancer that includes a Miniature Projection Head. The Miniature Projection Head may be operated in one of three modes, AFM, DBM, and RTM. The Miniature Projection Head projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein Enhancer may also be attached to a magnifying glass, a flat panel display, and the like.

Applicant believes that another reference corresponds to U.S. Pat. No. 9,044,207 issued to Goldman, et al. on Jun. 2, 2015 for Micro vein enhancer for use with a vial holder. However, it differs from the present invention because Goldman, et al. teach a Miniature Vein Enhancer that includes a Miniature Projection Head. The Miniature Projection Head may be operated in one of three modes, AFM, DBM, and RTM. The Miniature Projection Head projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein Enhancer may also be attached to a magnifying glass, a flat panel display, and the like.

Applicant believes that another reference corresponds to U.S. Pat. No. 9,061,109 issued to Wood, et al. on Jun. 23, 2015 for Vein scanner with user interface. However, it differs from the present invention because Wood, et al. teach a portable vein viewer apparatus that may be battery powered and hand-held to reveal patient vasculature information to aid in venipuncture processes. The apparatus comprises a first laser diode emitting infrared light, and a second laser diode emitting only visible wavelengths, wherein vasculature absorbs a portion of the infrared light causing reflection of a contrasted infrared image. A pair of silicon PIN photodiodes, responsive to the contrasted infrared image, causes transmission of a corresponding signal. The signal is processed through circuitry to amplify, sum, and filter the outputted signals, and with the use of an image processing algorithm, the contrasted image is projected onto the patient's skin surface using the second laser diode. Revealed information may comprise vein location, depth, diameter, and degree of certainty of vein locations. Projection of vein images may be a positive or a negative image. Venipuncture needles may be coated to provide visibility in projected images.

Applicant believes that another reference corresponds to U.S. Pat. No. 9,186,063 issued to Goldman, et al. on Nov. 17, 2015 for Scanned laser vein contrast enhancer using one laser for a detection mode and a display mode. However, it differs from the present invention because Goldman, et al. teach a miniature Vein Enhancer that includes a Miniature Projection Head. The Miniature Projection Head may be operated in one of three modes, AFM, DBM, and RTM. The Miniature Projection Head projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein Enhancer may also be attached to a magnifying glass, a flat panel display, and the like.

Applicant believes that another reference corresponds to U.S. Pat. No. 9,492,117 issued to Goldman, et al. on Nov. 15, 2016 for Practitioner-mounted micro vein enhancer. However, it differs from the present invention because Goldman, et al. teach a miniature Vein Enhancer that includes a Miniature Projection Head. The Miniature Projection Head may be operated in one of three modes, AFM, DBM, and RTM. The Miniature Projection Head projects an image of the veins of a patient, which aids the practitioner in pinpointing a vein for an intravenous drip, blood test, and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein Enhancer may also be attached to a magnifying glass, a flat panel display, and the like.

Applicant believes that another reference corresponds to U.S. Patent Application Publication No. 2012/0101342, published on Apr. 26, 2012 to Duffy, et al. for Pediatric tissue illuminator. However, it differs from the present invention because Duffy, et al. teach a pediatric tissue illuminator that includes a semi-rigid lighting head removably connected to a powered base unit for illuminating an infant's tissues while stabilizing a limb for venipuncture. The lighting head includes a series of LEDs and is placed behind an infant's arm, thereby directing light therethrough for enhanced viewing. A printed circuit board in the lighting head routes electrical conductors to the LEDs. A translucent soft covering is disposed between the printed circuit board and the infant's body. The base unit includes a control circuit for varying the application of electrical power to the lighting head via an electrical cable. Alternatively, a re-useable light head may be used with disposable semi-rigid housings.

Applicant believes that another reference corresponds to U.S. Patent Application Publication No 2012/0101343, published on Apr. 26, 2012 to Duffy, et al. for Medical imaging device. However, it differs from the present invention because Duffy, et al. teach a trans-illumination device that includes at least first and second sets of LEDs of two or more different colors arranged in a light head placed against a patient's skin. The LEDs are mounted to a printed circuit board in the light head. An electronic control circuit is coupled to the light head by an electrical cable to selectively operate the LEDs in two or more user-selected modes, with the ability to adjust the relative intensities of the different colors to best suit the physiology of the patient. The light head may have a U shape to surround an area of interest while providing ready access thereto. The light head may be used with a disposable, detachable cover having lenses for directing light from the LEDs into the patient's tissues.

Applicant believes that another reference corresponds to U.S. Patent Application Publication No. 2015/0094662, published on Apr. 2, 2015 to Lee, et al. for Visualization apparatus for vein. However, it differs from the present invention because Lee, et al. teach a visualization apparatus for the vein which includes a near-infrared ray irradiating unit for irradiating near-infrared rays below the skin of a target area, an infrared camera unit for photographing the target area, an image processing unit for receiving and processing image information of a portion below the skin of the target area, photographed by the infrared camera unit, and providing the processed image information to a display device, and a display device located near the target area to display the image information provided from the image processing unit.

Applicant believes that another reference corresponds to U.S. Pat. No. D362,910 issued to Frank C. Creaghan on Oct. 3, 1995 for Instrument for viewing subcutaneous venous structures. However, it differs from the present invention because Creaghan teaches a different ornamental design for an instrument for viewing subcutaneous venous structures.

Applicant believes that another reference corresponds to U.S. Pat. No. RE33,234 issued to Kim Landry on Jun. 19, 1990 for Transcutaneous intravenous illuminator. However, it differs from the present invention because Landry teaches a transcutaneous illuminating apparatus having a housing, which has a source of electrical energy, provided therein, a support removably mounted on one end of the housing having a plurality of arms pivotally supported thereby at their proximate ends, each of the arms having mounted on its distal end illuminating lights, an electrical circuit including the source of power and the illuminating lights, a switch for selectively completing the circuit between the illuminating lights and the source of electrical energy thereby activating the illuminating lights, and rheostats provided in the circuit for selectively varying the intensity of each of the illuminating lights.

Applicant believes that another reference corresponds to U.S. Pat. No. 6,923,762 issued on Aug. 2, 2005 to Creaghan, Jr. for Venoscope apparatus. However, it differs from the present invention because Creaghan teaches an improved instrument for viewing subcutaneous venous structure, known as a VENOSCOPE, which includes a clamshell housing, having a first fixed arm extending therefrom, and a second movable arm captured by upper and lower portions of the housing; a first high intensity plurality of white and red LEDs positioned at the end of the first arm, and a second high intensity plurality of high intensity red and white LED positioned at the end of the second arm, and a battery positioned within the housing for selectively provided electrical energy to the red and white LEDs, so that a more defined and intensely illuminated field of visualization between structures below the skin and the surrounding subcutaneous tissue is defined. Additional embodiments include a tube or handle connected to a head having multiple arms or a single arm with multiple LEDs.

Other patents describing the closest subject matter provide for a number of more or less complicated features that fail to solve the problem in an efficient and economical way. None of these patents suggest the novel features of the present invention.

SUMMARY OF THE INVENTION

The present invention is a portable breast light assembly, comprising a housing having a sidewall. The sidewall comprises at least one ventilation hole. An electrical assembly comprises a control panel having a power switch, a timer controller, an intensity controller, a screen, and at least one light source to emit visible light at a predetermined wavelength. The present invention further comprises a cap assembly.

The housing further comprises a top edge and a base. The sidewall further comprises first and second protrusions. The timer controller controls at least one range of operating time. The intensity controller controls at least one level of light intensity. The electrical assembly comprises a sensor. The sensor is connected to circuitry that is connected to the at least one light source. The predetermined wavelength is approximately between 620-780 nm corresponding to a red light region. The electrical assembly comprises a port that receives a plug connector to receive charge from an external source.

The cap assembly comprises a cap edge, a base edge, a cap base and a cap sidewall. The cap base comprises at least one hole. The at least one light source aligns with the at least one hole. The cap sidewall has a first predetermined diameter. The base edge has a second predetermined diameter. The cap sidewall extends from the base edge, and the first predetermined diameter is smaller than the second predetermined diameter.

The cap assembly comprises a cover. The cover is positioned onto the cap base. The cover is secured by the cap edge. The cover contacts the sensor. The cover is transparent to allow the visible light to pass therethrough. The base edge is fixed onto the top edge of the housing. The light emitted by the at least one light source illuminates a breast when the cover is biased against the breast with a predetermined force.

It is therefore one of the main objects of the present invention to provide a portable breast light assembly.

It is another object of this invention to provide a portable breast light assembly designed for light transmission through breast tissue.

It is another object of this invention to provide a portable breast light assembly for breast viewing.

It is another object of this invention to provide a portable breast light assembly that is volumetrically efficient for carrying, transporting, and storage.

It is another object of this invention to provide a portable breast light assembly, which is of a durable and reliable construction.

It is yet another object of this invention to provide a portable breast light assembly that maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
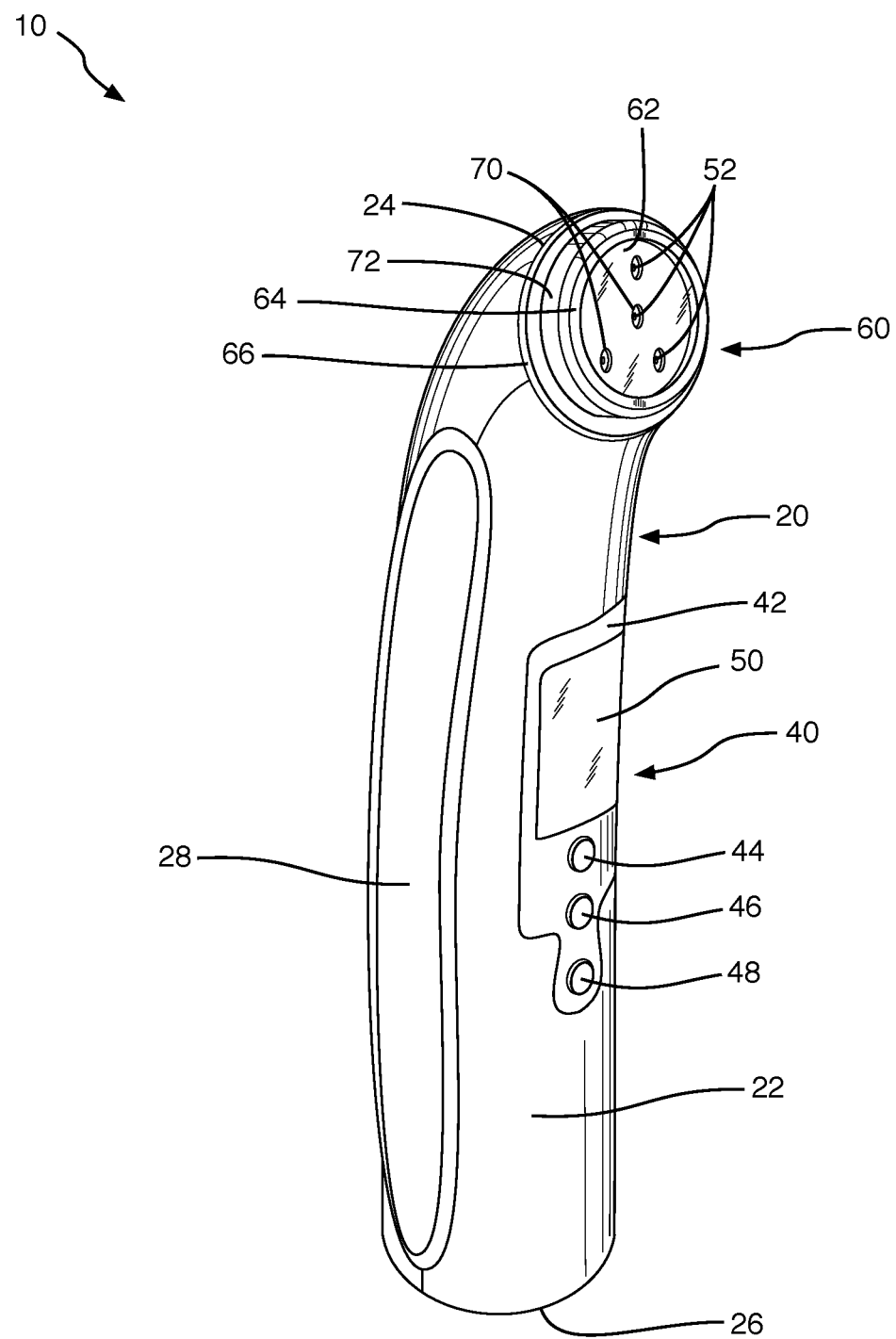
FIG. 1 is an isometric view of the present invention.

Referring now to the drawings, the present invention is a portable breast light assembly and is generally referred to with numeral 10. It can be observed that it basically includes housing 20, electrical assembly 40, and cap assembly 60.

Figure 2:
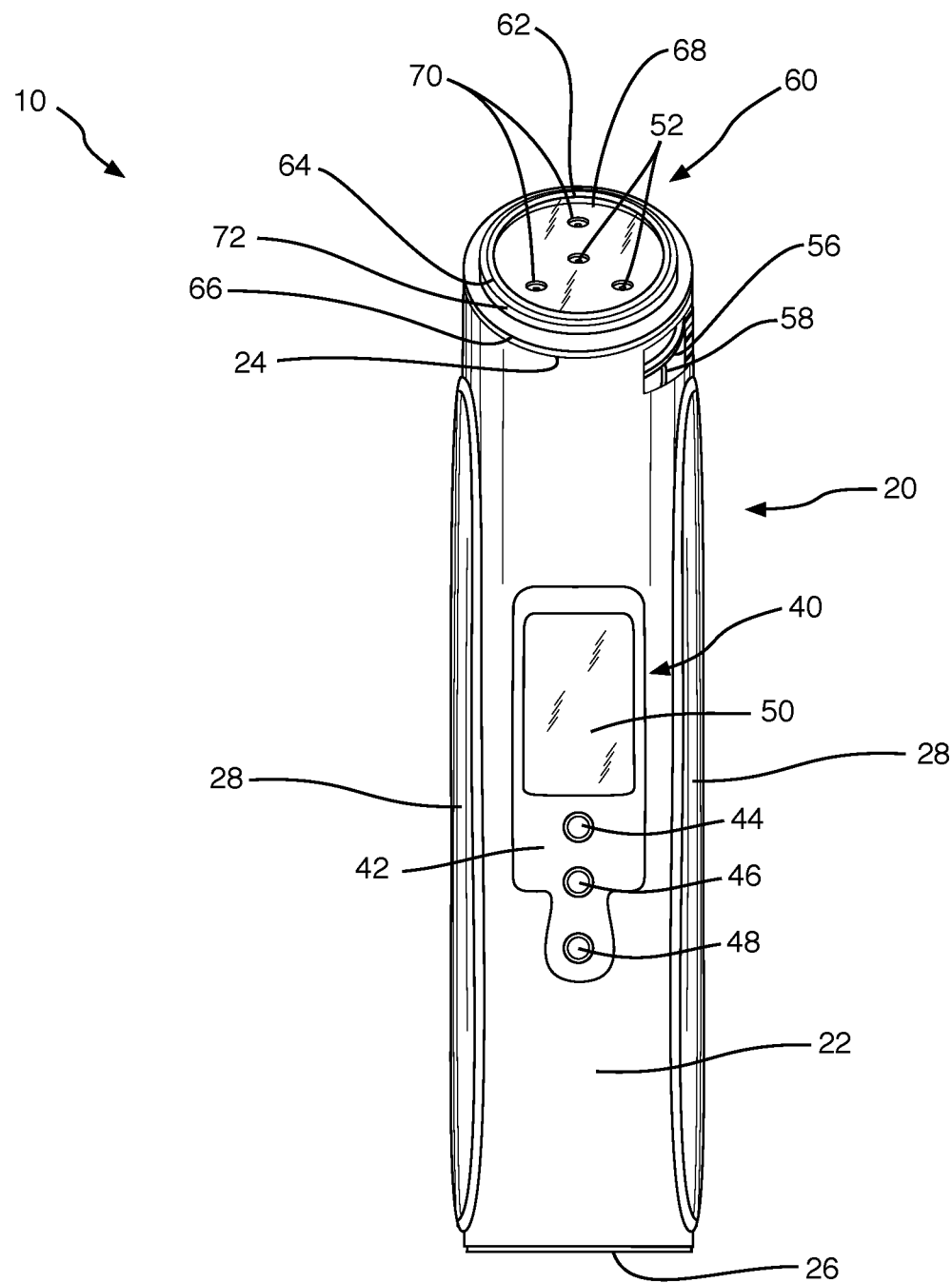
FIG. 2 is a front view of the present invention with a cut view at the cap assembly and housing.

As seen in FIGS. 1 and 2, housing 20 has sidewall 22 that comprises top edge 24 and base 26. Sidewall 22 further comprises at least one ventilation hole 30, seen in FIG. 3.

As also seen in FIGS. 1 and 2, electrical assembly 40 comprises control panel 42 having power switch 44, timer controller 46, intensity controller 48, screen 50, at least one light source 52, and a rechargeable battery, not seen. Power switch 44 is an on/off switch. Timer controller 46 controls at least one range of operating time. In a preferred embodiment, there are two different ranges of operating time. As an example the operating times may be 2 or 5 minutes. It is noted however that the operating times may be lesser or greater. Intensity controller 48 controls at least one level of light intensity. In a preferred embodiment, there are four different intensity levels. The light intensity level is incremented or reduced to optimally illuminate a breast when cover 62 is biased against a breast with a predetermined force. The light intensity level may depend on factors such as, but not limited to, the size and firmness of the breast.

In a preferred embodiment, screen 50 is a liquid-crystal display that turns on when power switch 44 is in the "on" position. Screen 50 shows a status of parameters including operating time, intensity level, and battery charge.

At least one light source 52 emits visible light at a predetermined wavelength. In a preferred embodiment, the predetermined wavelength is approximately between 620-780 nm corresponding to a red light region. At least one light source 52 may be a plurality of light-emitting diodes (LED).

Cap assembly 60 comprises cap edge 64, base edge 66, cap base 68, and cap sidewall 72. Base edge 66 is fixed to top edge 24 of housing 20. Cap base 68 comprises at least one hole 70. Each of at least one light source 52 aligns with holes 70. In a preferred embodiment, there are four holes 70 with respective light sources 52. In addition, cap sidewall 72 has a first predetermined diameter. Base edge 66 has a second predetermined diameter. Cap sidewall 72 extends from base edge 66. The first predetermined diameter is smaller than the second predetermined diameter. Cover 62 is positioned onto cap base 68 and is secured by cap edge 64. Cover 62 is transparent to allow the visible light to pass therethrough.

As seen in FIG. 2, housing 20 further comprises first and second protrusions 28 for easier handling and/or gripping. Control panel 42 is positioned between first and second protrusions 28.

Electrical assembly 40 further comprises sensor 56. Sensor 56 is connected to circuitry 58 that is connected to at least one light source 52.

Circuitry 58 is a touch detection circuitry that is connected with a single chip computer, which has a built-in debounce circuitry. Circuitry 58 comprises a touch input contact connected to sensor 56 and a touch output contact connected to at least one light source 52. Cover 62 contacts sensor 56 by pressure or a predetermined force.

When cover 62 touches the skin, such as when cover 62 is biased against a breast with a predetermined force, the touch output contact outputs a higher intensity of light.

When cover 62 does not touch the skin, such as when cover 62 is not biased against a breast, the touch output contact outputs a lower intensity of light. Therefore the light intensity changes from lower to higher by skin contact due to sensor 56.

Figure 3:
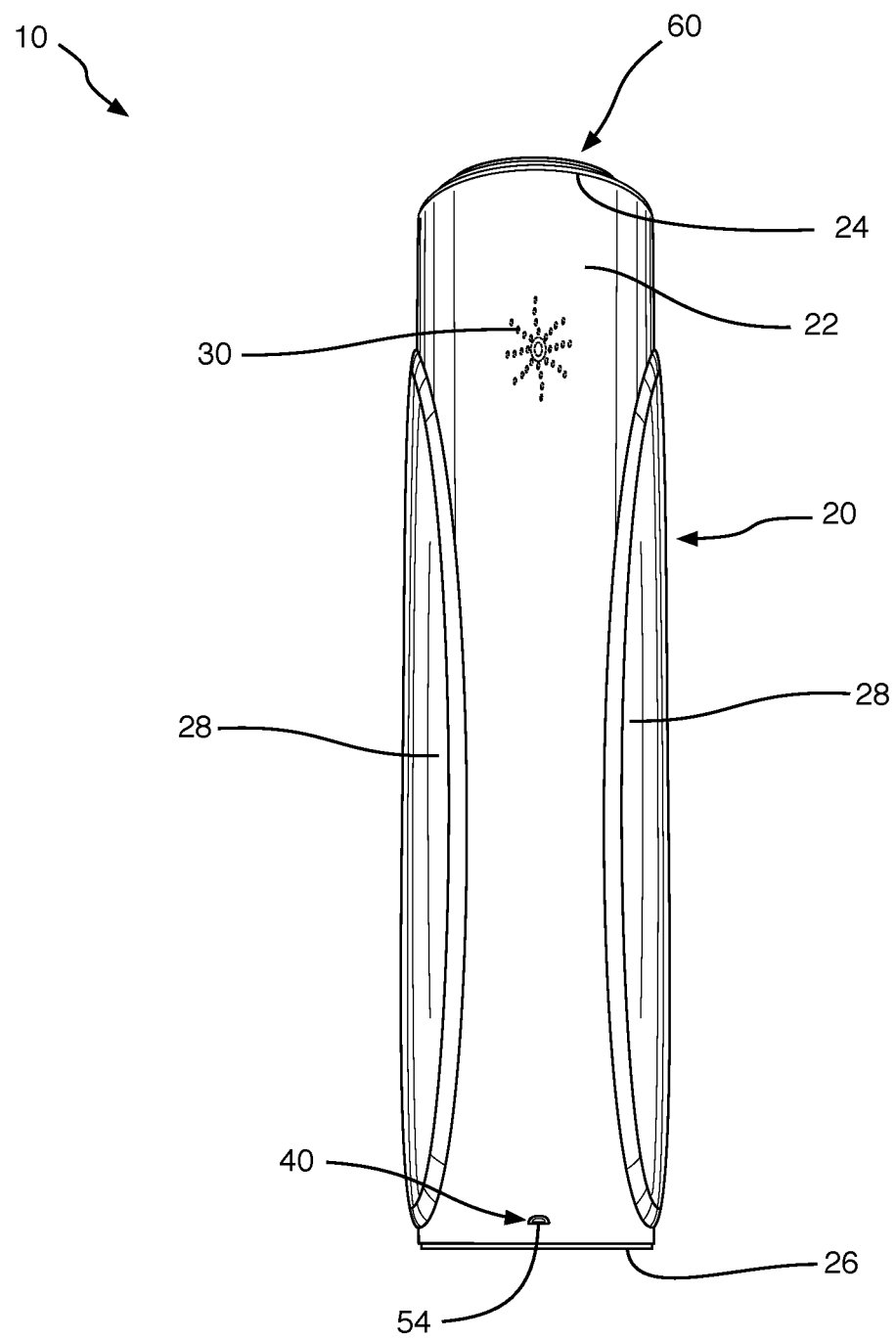
FIG. 3 is a rear view of the present invention.

As seen in FIG. 3, sidewall 22 has at least one ventilation hole 30. Due to electrical assembly 40, and particularly light sources 52 seen in FIGS. 1 and 2, portable breast light assembly 10 may become warm during usage. Ventilation holes 30 are designed to counteract this effect. In a preferred embodiment, there are a predetermined number of ventilation holes 30 near cap assembly 60. Electrical assembly 40 further comprises port 54 that receives a plug connector, not seen, to receive charge from an external source.

Figure 4:
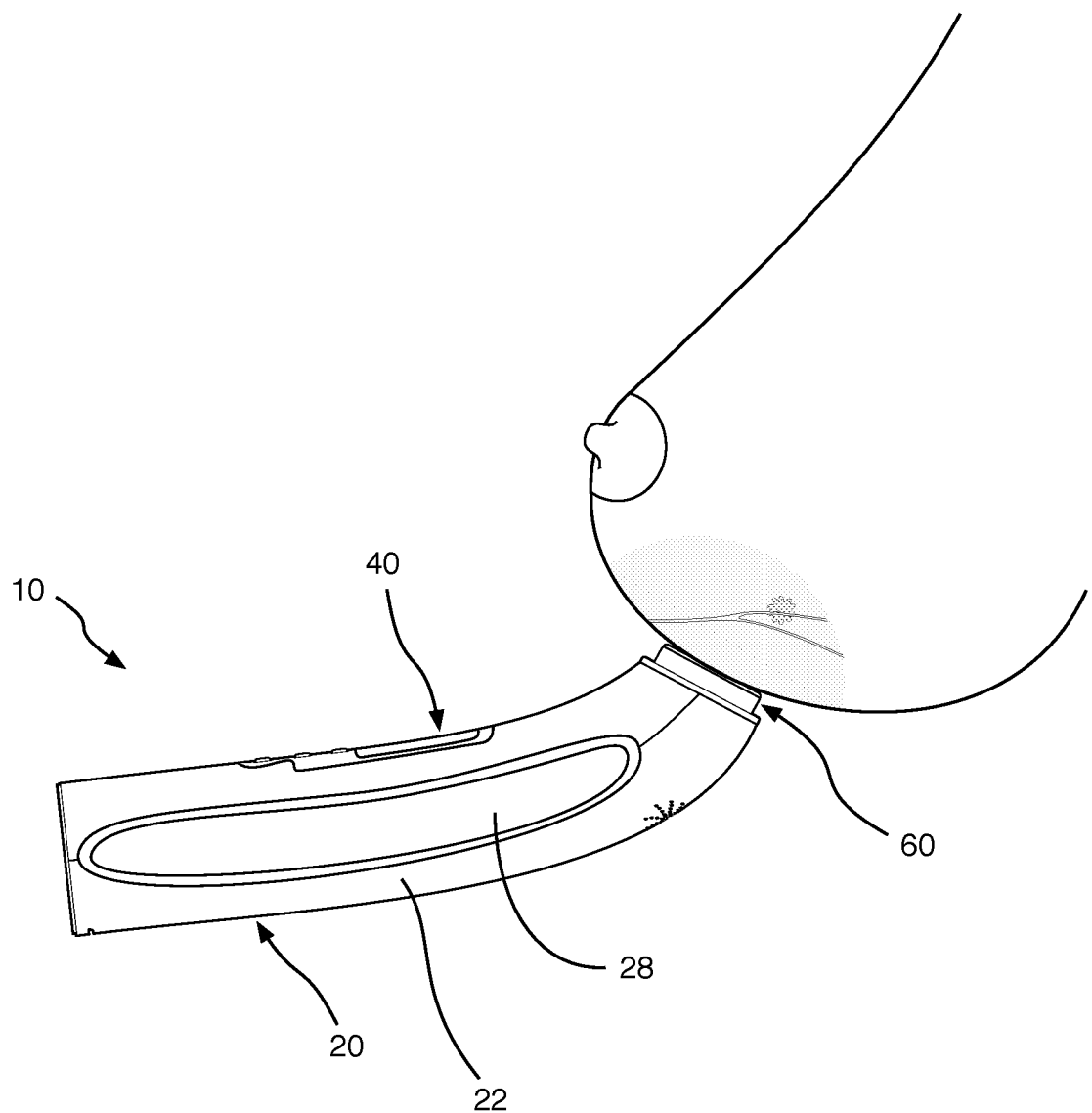
FIG. 4 is a view of the present invention in use illuminating a breast.

As seen in FIG. 4, light emitted by at least one light source 52, seen in FIGS. 1 and 2, illuminates a breast when cover 62 is biased against the breast with a predetermined force. Portable breast light assembly 10 is therefore designed to maximize light transmission through breast tissue. Therefore, present invention 10 works by shining a powerful red light through the breast tissue, whereby the predetermined wavelength of the red light is approximately between 620-780 nm corresponding to a red light region. As a result, one can see veins and blood vessels. Around the nipple, one may also see small dots, which are part of the mammary glands.

For optimal use of present invention 10:
A) charge portable breast light assembly 10 before use;
B) make a room as dark as possible. The darker the room, the easier to use portable breast light assembly 10. Wait a few minutes to allow the eyes to get used to the dark. Turn on portable breast light assembly 10;
C) for each breast: lubricate a breast to allow cover 62 to slide across the breast more easily. Apply the lubricant liberally over the entire breast. In a preferred embodiment, utilize water-based lubricants;
D) in front of a mirror while standing or sitting, hold and keep portable breast light assembly 10 against the breast with a predetermined force. The breast itself will suddenly appear brighter. Dark lines are veins and other blood vessels are in silhouette; and
E) slide portable breast light assembly 10 around the breast while keeping the portable breast light assembly 10 against the breast with the predetermined force.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:
1. A portable breast light assembly, consisting of:
A) a housing having a sidewall, said sidewall has at least one ventilation hole and first and second protrusions, said housing further has a top edge and a base;
B) an electrical assembly having a control panel that is positioned between said first and second protrusions that are for handling and gripping, said control panel also having a power switch that is an on/off switch, a timer controller, an intensity controller, a screen, and at least one light source that is a plurality of light-emitting diodes to emit visible light at a predetermined wavelength, said screen is a liquid-crystal display that turns on when said power switch is in an on position, said timer controller controls at least one range of operating time, and said screen shows a status of said operating time, said intensity controller controls at least one level of light intensity, and said screen shows a status of said light intensity and battery charge, said electrical assembly further has a sensor, said sensor is connected to circuitry that is connected to said at least one light source, said circuitry is a touch detection circuitry that is connected with a single chip computer, which has a built-in debounce circuitry, said circuitry has a touch input contact connected to said sensor and a touch output contact connected to said at least one light source, said touch output contact outputs at least two light intensities, wherein one is larger than the other, whereby said predetermined wavelength is between 620-780 nm corresponding to a red light region, whereby said electrical assembly further has a port that receives a plug connector to receive charge from an external source; and
C) a cap assembly having a cap edge, a base edge, a cap base and a cap sidewall, said cap base has at least one hole, at least one light source aligns with said at least one hole, said cap sidewall has a first predetermined diameter, said base edge has a second predetermined diameter, said cap sidewall extends from said base edge, and said first predetermined diameter is smaller than said second predetermined diameter, cap assembly further has a cover that is positioned onto said cap base and is secured by said cap edge, said cover contacts said sensor by pressure or a predetermined force, and said cover is transparent to allow said visible light to pass therethrough, and said base edge is fixed onto said top edge of said housing, said at least one hole are four holes that aligns with four of said at least one light source respectively, said screen is a first predetermined distance from said cap assembly, said power switch is a second predetermined distance from said cap assembly, and said second predetermined distance is greater than said first predetermined distance, and said timer controller is a third predetermined distance from said cap assembly, and said third predetermined distance is greater than said second predetermined distance, and said intensity controller is a fourth predetermined dis- tance from said cap assembly, and said fourth predetermined distance is greater than said third predetermined distance;

wherein said portable breast light assembly is further configured to increment or reduce said at least one level of light intensity to illuminate a breast, whereby said visible light emitted by said at least one light source illuminates said breast when said cover is biased against said breast with said predetermined force, whereby said touch output contact outputs a higher intensity of said visible light to enable light transmission through breast tissue to see veins, blood vessels, and part of mammary glands, and when said cover is not biased against said breast, said touch output contact outputs a lower intensity of said visible light, and said light intensity level depends on a size and firmness of said breast, said veins and said blood vessels appear in silhouette when said cover is biased against said breast with said predetermined force, and bias said cover against said breast with said predetermined force, after application of a water-based lubricant to said breast.

\* \* \* \* \*